(12) United States Patent
Jain

(10) Patent No.: US 12,072,950 B1
(45) Date of Patent: Aug. 27, 2024

(54) UNIFIED DYNAMIC OBJECTS GENERATED FOR WEBSITE INTEGRATION

(71) Applicant: DOCEREE INC., Parsippany, NJ (US)

(72) Inventor: Harshit Jain, Parsippany, NJ (US)

(73) Assignee: DOCEREE INC., Parsippany, NJ (US)

( * ) Notice: Subject to any disclaimer, the term of this patent is extended or adjusted under 35 U.S.C. 154(b) by 0 days.

(21) Appl. No.: 18/379,056

(22) Filed: Oct. 11, 2023

Related U.S. Application Data

(63) Continuation-in-part of application No. 18/116,290, filed on Mar. 1, 2023, now Pat. No. 11,869,673.

(51) Int. Cl.
 *G06F 17/00* (2019.01)
 *G06F 16/957* (2019.01)
 *G06F 16/958* (2019.01)

(52) U.S. Cl.
 CPC ........ *G06F 16/986* (2019.01); *G06F 16/9577* (2019.01)

(58) Field of Classification Search
 CPC ........................... G06F 16/986; G06F 16/9577
 See application file for complete search history.

(56) References Cited

U.S. PATENT DOCUMENTS

| | | | | |
|---|---|---|---|---|
| 7,165,218 B1 * | 1/2007 | Hancock | ............... | G06F 16/958 709/204 |
| 7,676,505 B2 * | 3/2010 | Chess | ................... | G06F 16/954 707/999.203 |
| 9,483,571 B2 * | 11/2016 | Bertram | ................ | G06F 16/958 |
| 9,773,264 B2 * | 9/2017 | Brown | ............... | G06Q 30/0601 |
| 9,923,901 B2 * | 3/2018 | Schneider | ........... | G06F 16/2379 |
| 9,934,204 B2 * | 4/2018 | Bertram | ................ | G06F 40/221 |
| 9,984,125 B1 * | 5/2018 | Smith | ................ | G06F 16/24568 |
| 10,049,141 B2 * | 8/2018 | Prophete | ............. | G06F 16/2455 |
| 10,089,368 B2 * | 10/2018 | Pominville | ....... | G06F 16/90328 |
| 10,101,889 B2 * | 10/2018 | Prophete | ............. | G06F 3/04842 |
| 10,114,805 B1 * | 10/2018 | Root | ..................... | G06F 40/143 |
| 10,115,213 B2 * | 10/2018 | Prophete | ................. | G06F 21/53 |

(Continued)

*Primary Examiner* — Mohammed H Zuberi
(74) *Attorney, Agent, or Firm* — Edmond DeFrank

(57) ABSTRACT

The embodiments disclose a dynamic unified object generation platform, including a dynamic unified object generation computer server coupled to at least a first partner and a second partner and configured to electronically receive and store in a server database at least a first set of rules from the first partner and a second set of rules from the second partner for a publisher website, a server processor coupled to the server database and configured to automatically and dynamically create a comparison between a unified set of rules and the first set of rules and the second set of rules, a pre-deployment processor coupled to the server processor and configured to dynamically convert the comparison into a single unified code structure based on the unified set of rules, a post-deployment processor coupled to the pre-deployment processor and configured to dynamically integrate the single unified code structure into the publisher website as a unified rule set to control at least two predetermined operational aspects of the publisher website based on the first and second set of rules and at least one graphical user interface configured to display to a publisher user of the publisher website at least one operational aspect controlled by the unified rule set.

20 Claims, 10 Drawing Sheets

(56) References Cited

U.S. PATENT DOCUMENTS

| | | | | |
|---|---|---|---|---|
| 10,277,665 B1* | 4/2019 | Vidyananda | .......... | G06F 16/958 |
| 10,311,047 B2* | 6/2019 | Gitelman | ............... | G06F 16/283 |
| 10,649,745 B1* | 5/2020 | Patel | ........................ | G06F 8/71 |
| 10,671,751 B2* | 6/2020 | Schneider | ............. | G06F 16/254 |
| 10,698,704 B1* | 6/2020 | Patel | ..................... | G06F 16/955 |
| 10,705,805 B1* | 7/2020 | Bosworth | ............. | G06F 40/186 |
| 10,719,202 B2* | 7/2020 | Pankaj | ................... | G06Q 40/06 |
| 10,846,436 B1* | 11/2020 | Pham | ............... | G06K 19/06037 |
| 10,893,008 B2* | 1/2021 | Krishnaswamy | ....... | G06F 9/451 |
| 11,334,897 B2* | 5/2022 | Rathod | ................... | G06F 16/58 |
| 2002/0059054 A1* | 5/2002 | Bade | ...................... | G06F 30/33 |
| | | | | 703/20 |
| 2007/0185927 A1* | 8/2007 | Chess | ................... | G06F 16/954 |
| | | | | 707/999.203 |
| 2007/0271145 A1* | 11/2007 | Vest | ................... | G06Q 30/0276 |
| | | | | 705/14.72 |
| 2010/0063882 A1* | 3/2010 | Danieli | ................ | G06F 40/134 |
| | | | | 705/14.61 |
| 2014/0047413 A1* | 2/2014 | Sheive | ...................... | G06F 8/33 |
| | | | | 717/110 |
| 2014/0157106 A1* | 6/2014 | Bertram | ................ | G06F 40/143 |
| | | | | 715/234 |
| 2014/0258968 A1* | 9/2014 | Brown | .................. | G06Q 10/06 |
| | | | | 717/103 |
| 2014/0258969 A1* | 9/2014 | Brown | ..................... | G06F 8/30 |
| | | | | 717/103 |
| 2017/0317898 A1* | 11/2017 | Candito | ................. | H04L 63/08 |
| 2023/0026368 A1* | 1/2023 | Silverstein | ............ | G06F 16/986 |

* cited by examiner

UNIFIED DYNAMIC OBJECTS GENERATED FOR WEBSITE INTEGRATION

CROSS-REFERENCE TO RELATED APPLICATIONS

This Patent Application is a Continuation-in-part and claims priority to the United States Patent Application entitled: "ELECTRONIC HEALTH RECORD PLATFORM", U.S. Ser. No. 18/116,290 filed on Mar. 1, 2023, by Harshit Jain, which is incorporated herein by reference.

BACKGROUND

Publisher monetization requires the deployment of multiple components for delivering the best end-user experience. To do so, a publisher may need to integrate with multiple technologies and data partners and in the process enable numerous disparate business components such as data collection, ad serving, data partner sync, identity partner sync, viewability, and so on to be integrated into their website (publisher's website).

Because the complexity of coding is time and resource-intensive and more often than not requires frequent maintenance and upgradation, the publisher either utilizes the expertise of their tech team or enters into service contracts with third-party vendors for each of these integrations. Even seemingly simple customizations to meet new business requirements could become cumbersome with an ever-increasing line of their codebase.

Thus, publishers anticipate a solution in which their specific business needs are met by a simple solution that is easy to deploy and much easier to customize.

BRIEF SUMMARY OF THE INVENTION

The embodiments of the present invention include a dynamic unified object generation platform having a dynamic unified object generation computer server coupled to at least a first partner and a second partner and configured to electronically receive and store in a server database at least a first set of rules from the first partner and a second set of rules from the second partner for a publisher website, a server processor coupled to the server database and configured to automatically and dynamically create a comparison between a unified set of rules and the first set of rules and the second set of rules, a pre-deployment processor coupled to the server processor and configured to dynamically convert the comparison into a single unified code structure based on the unified set of rules, a post-deployment processor coupled to the pre-deployment processor and configured to dynamically integrate the single unified code structure into the publisher website as a unified rule set to control at least two predetermined operational aspects of the publisher website based on the first and second set of rules and at least one graphical user interface configured to display to a publisher user of the publisher website at least one operational aspect controlled by the unified rule set.

The embodiments of the present invention include a unified dynamic object framework that uses a unified dynamic object code from a single unified codebase. The single unified codebase accepts a broad range of components of publisher partners to be entered into the single unified codebase. The unique unified dynamic object framework codebase unifies all of the diverse components dynamically with discrete technical configurations of the publisher partners. The unified dynamic object framework brings together and unifies all of the components through seamless publisher partner integrations.

The process allows publisher partners to utilize the unified dynamic object framework and generate the code required to specifically unique requirements. The process is defined in two distinct phases, a pre-deployment phase where a publisher partner utilizes the unified dynamic object framework to obtain the required dynamic object for deployment on their respective website. The pre-deployment phase is followed by a post-deployment phase. The post-deployment phase is utilized to create dynamic objects on the publisher's website that are then integrated into the unified dynamic object framework. The dynamic objects that are created using the unified dynamic object framework are utilized with them being integrated into the publisher's site. The post-deployment phase is utilized to create dynamic objects on the unified dynamic object framework that are then integrated into the publisher's website.

DETAILED DESCRIPTION OF THE INVENTION

In the following description, reference is made to the accompanying drawings, which form a part hereof, and which are shown by way of illustration a specific example in which the invention may be practiced. It is to be understood that other embodiments may be utilized and structural changes may be made without departing from the scope of the present invention.

General Overview

It should be noted that the descriptions that follow, for example, in terms of automated unified dynamic objects generated for website integration are described for illustrative purposes and the underlying system can apply to any number and multiple types of operating systems. In one embodiment of the present invention, the automated unified dynamic objects generated for website integration can be configured using a dynamic object feature set. The automated unified dynamic objects generated for website integration can be configured to include a publisher and can also be configured to include an automated dynamic object generator using the present invention.

Figure 1A:
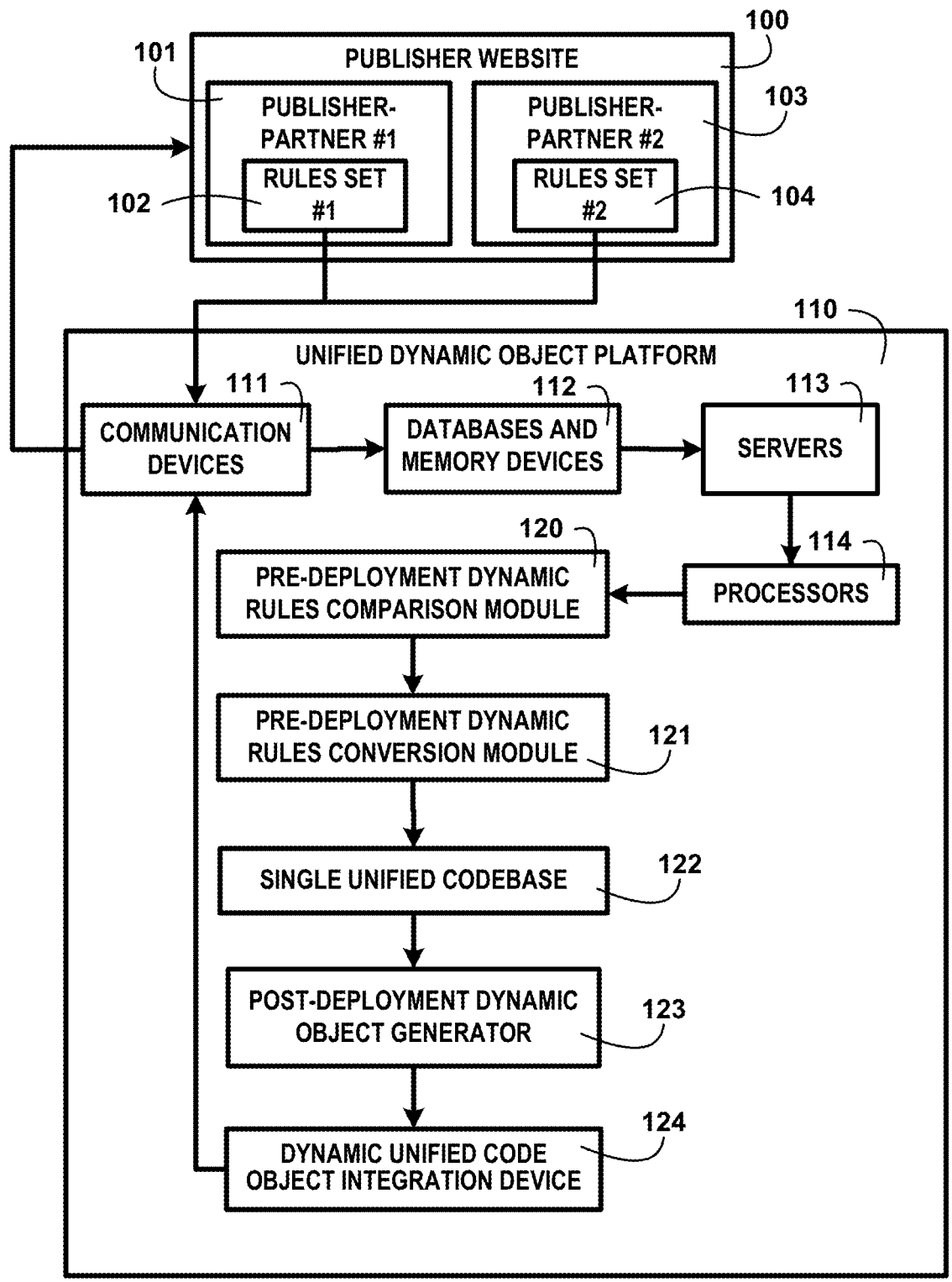
FIG. 1A shows a block diagram of an overview of a unified dynamic object platform of one embodiment.

FIG. 1A shows a block diagram of an overview of a unified dynamic object platform of one embodiment. FIG. 1A shows a publisher website 100 containing a publisher-partner #1 101 rules set #1 102 and a publisher-partner #2 103 rules set #2 104. The rules sets are selected by the publisher and transmitted to a unified dynamic object platform 110 using communication devices 111. The communication devices 111 store the multiple rules sets in platform databases and memory devices 112. Multiple platform servers 113 use multiple processors 114 to use at least one pre-deployment dynamic rules comparison module 120 to dynamically compare the multiple rules sets to identify the code structures. The multiple processors 114 use at least one pre-deployment dynamic rules conversion module 121 to dynamically convert the multiple rules sets into a single unified codebase 122. At least one post-deployment dynamic object generator 123 is used to automatically generate dynamic objects to unify the multiple rules sets code structures to operate in conjunction as a unified codebase. A dynamic unified code object integration device 124 transmits the unified codebase using the communication devices 111 to integrate the unified codebase into the publisher website 100 of one embodiment.

Figure 1B:
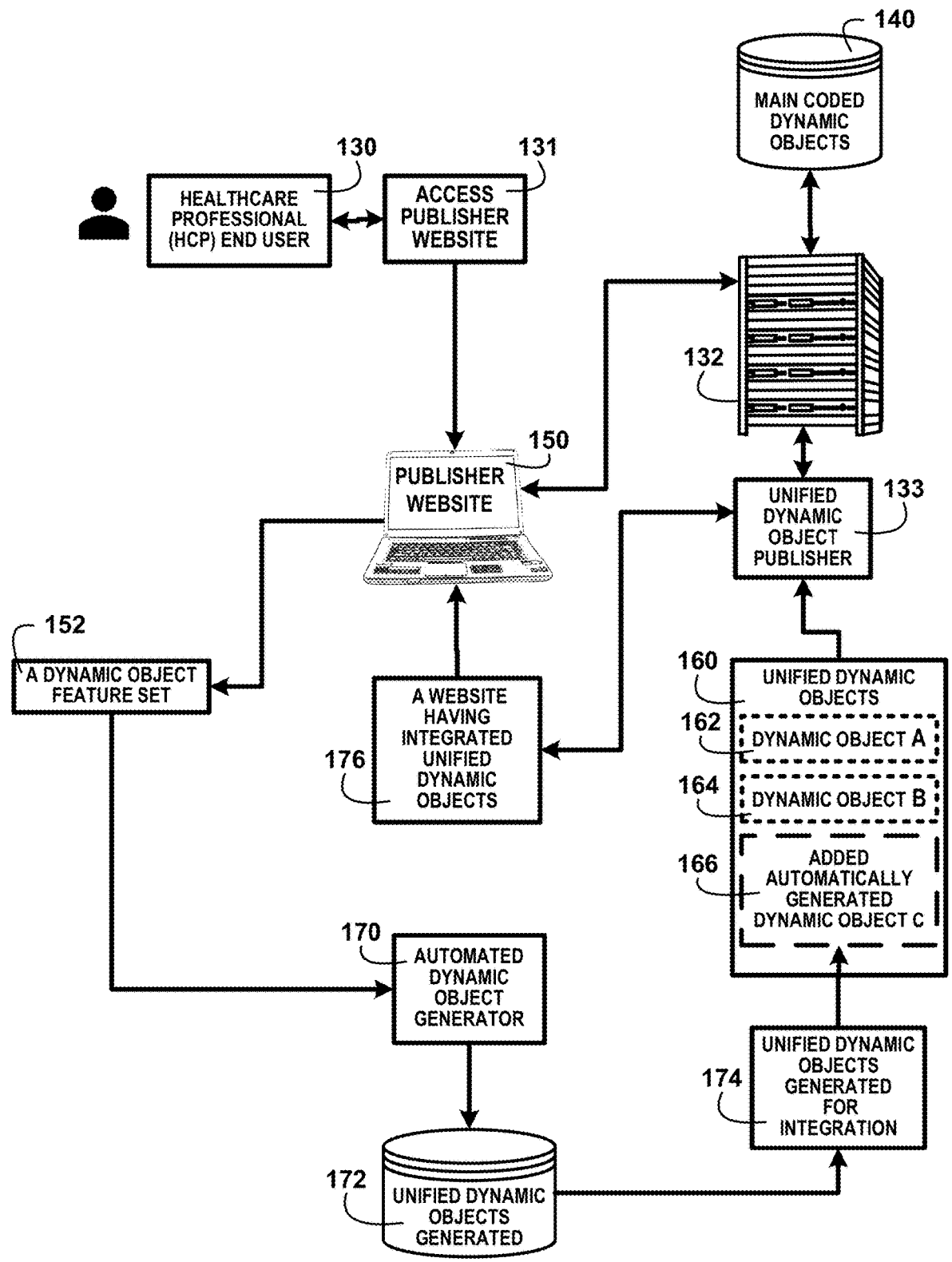
FIG. 1B shows for illustrative purposes only an example of automated unified dynamic objects generated for website integration of one embodiment.

FIG. 1B shows for illustrative purposes only an example of automated unified dynamic objects generated for website integration of one embodiment. FIG. 1B shows a healthcare professional (HCP) end user 130 logging in to access publisher website 131. The server 132 has loaded main coded dynamic objects 140 to the publisher website 150. The end user access to the publisher website 150 does not trigger directly any creation of unified dynamic objects 160.

Main coded dynamic objects 140 are loaded into the publisher website 150. The activity of the HCP itself triggers a request to the publisher. The HCP could be browsing the site casually reading the content or even signing up for some newsletter on the said site. The activity of the HCP itself triggers a response from the main coded dynamic objects, which understand the HCP events on the site and based on the integrated dynamic objects in the website provide the apt feature set thereof. The user does not have any activity in generating code.

At least one dynamic object feature set 152 can be selected by the publisher and loaded into the automated dynamic object generator 170. The new automated unified dynamic objects generated 172 are finished code automatically created based on the selected features. The automated unified dynamic objects generated for integration 174 are integrated into the unified dynamic objects 160 including coded dynamic object A 162 and dynamic object B 164 and now include added automatically generated dynamic object C 166.

The unified dynamic objects are fully integrated using the unified dynamic object publisher 133 and stored on server 132 for future access on the publisher website 150 by the particular HCP. Simultaneously the unified dynamic object publisher 133 uploads the expanded dynamic objects to the publisher website 150 having integrated unified dynamic objects 176. The dynamic object feature set 152 and rules are embedded dynamically in the automated dynamic object generator 170 which are created automatically based on a unified dynamic object publisher 133 selection, thereby discarding the cumbersome and error-prone process of innumerable customizations and coding of one embodiment.

DETAILED DESCRIPTION

Figure 2:
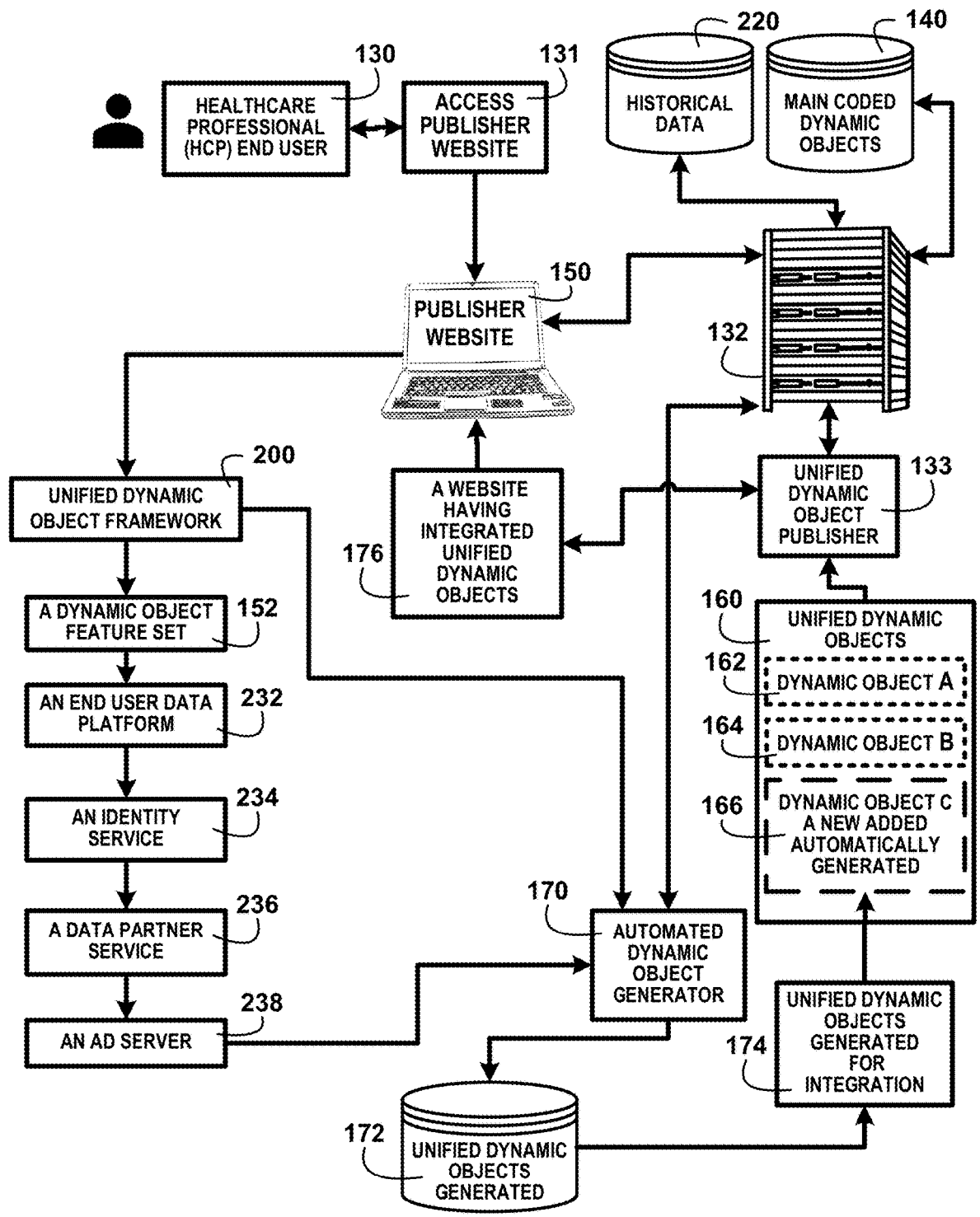
FIG. 2 shows for illustrative purposes only an example of a dynamic object feature set of one embodiment.

FIG. 2 shows for illustrative purposes only an example of a dynamic object feature set of one embodiment. FIG. 2 shows the healthcare professional (HCP) end user 130 logging in to access publisher website 131. The publisher website 150 wirelessly connects to server 132 containing a unified dynamic object framework 200. The unified dynamic object framework 200 architecture contains the dynamic object features and components allowing publishers to maintain and modify the functions of the publisher website 150. For example, the unified dynamic object framework 200 supports geographical or location-centric publisher partner synchronizations. The server 132 has loaded main coded dynamic objects 140 to the publisher website 150. Additionally, historical data 220 stored on a database is made available to the unified dynamic object publisher 133.

Once the HCP logs into a publisher website 150 for consultation, research, or any other content consumption, the publisher website 150 connects to a CDN (content delivery network) server 132 to obtain the unified dynamic objects that contain the dynamic object features and components. This unified dynamic object then enables requisite functions on the website and consolidates a request to achieve website functions. The unified dynamic object framework empowers the website to select the right set of dynamic object feature sets into the automated dynamic object generator for the generator to synthesize the desired set of functionality into auto-created unified dynamic objects.

At least one dynamic object feature set 152 can be selected and loaded into the automated dynamic object generator 170. In one embodiment at least one dynamic object feature set 152 includes an end-user data platform 232, an identity service 234, a data partner service 236, and an ad server 238. Every new Publisher is provided with a unique set of feature components configured for them to meet their specific requirements. The unique identity service 234 utilizes an identity partner sync seamlessly added to the unified dynamic object. It also means users can effortlessly maintain the existing unified dynamic object framework 200 and do not need to make additional changes in every dynamic object designed for integrated publisher partners.

The new automated unified dynamic objects generated 172 are finished code automatically created based on the selected features. The automated unified dynamic objects generated for integration 174 are integrated into the unified dynamic objects 160 including coded dynamic object A 162 and dynamic object B 164 and now include added automatically generated dynamic object C 166.

The unified dynamic objects are fully integrated using the unified dynamic object publisher 133 and stored on server 132 for future use on the publisher website 150. Simultaneously the unified dynamic object publisher 133 uploads the expanded dynamic objects to the publisher website 150 having integrated unified dynamic objects 176. The dynamic object feature set 152 and rules are embedded dynamically in the automated dynamic object generator 170 which are created automatically based on unified dynamic object publisher 133 selection, thereby discarding cumbersome and error-prone process of innumerable customizations and coding of one embodiment.

Figure 3:
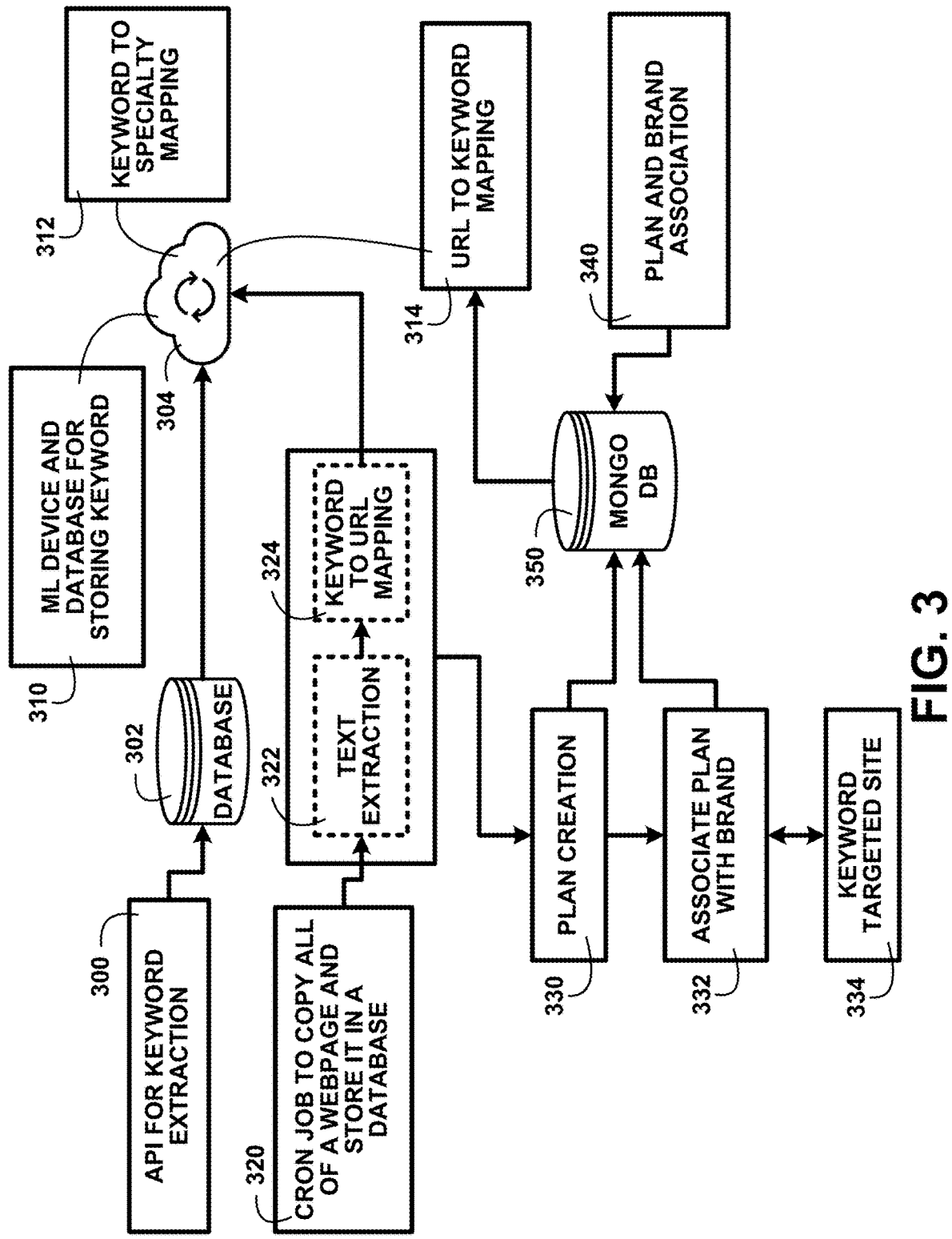
FIG. 3 shows for illustrative purposes only an example of a ML model and database storing keyword to specialty mapping of one embodiment.

ML Model and Database Storing Keyword to Specialty Mapping:

FIG. 3 shows for illustrative purposes only an example of a ML model and database storing keyword to specialty mapping of one embodiment. FIG. 3 shows an API for keyword extraction and refinement (parse data from XML level-wise) 300. The application programming interface (API) stores the data in a database 302 and transmits the data to a cloud 304. The data transmitted to Cloud 304 is parsed using a machine learning (ML) device. A machine learning device is a system that uses data and algorithms to determine associations between words, phrases, and data to formulate an explanation of objects, and facts to analyze and draw inferences from patterns in data. Machine learning is a branch of artificial intelligence.

The ML device and database are used for storing keywords for specialty mapping 310. The keyword to specialty mapping is stored in cloud 312 for dynamic object descriptions. The Uniform resource locator (URL) is used in dynamic object descriptions. URL to keyword mapping is stored in the cloud (CRON job runs once daily) 314. A cron job is a task that is scheduled to run periodically. Users can use the cron command-line utility or the crontab file to specify commands or scripts to run at fixed times, dates, or intervals. Cron jobs are often used for running backups, monitoring disk space, deleting files, and other system maintenance tasks. Cron job is used to copy all or a portion of a webpage and store it in a database and is run once daily to update adding new webpages viewed 320. The CRON job performs text extraction 322 and keyword-to-URL mapping 324 for dynamic object descriptions and integration. The text extraction 322 and keyword to URL mapping 324 functions include plan creation 330, associate plan with brand 332, and serve keyword targeted site 334. The plan and brand association 340 are stored in Mongo DB 350. The Mongo DB 350 data is converted into URL to keyword mapping stored in the cloud (cron job runs once daily) 314 of one embodiment. To crawl the page as used herein means to create a list of webpages visited, store copies of the webpages in a database, and create an index of the websites searched by the user.

Figure 4:
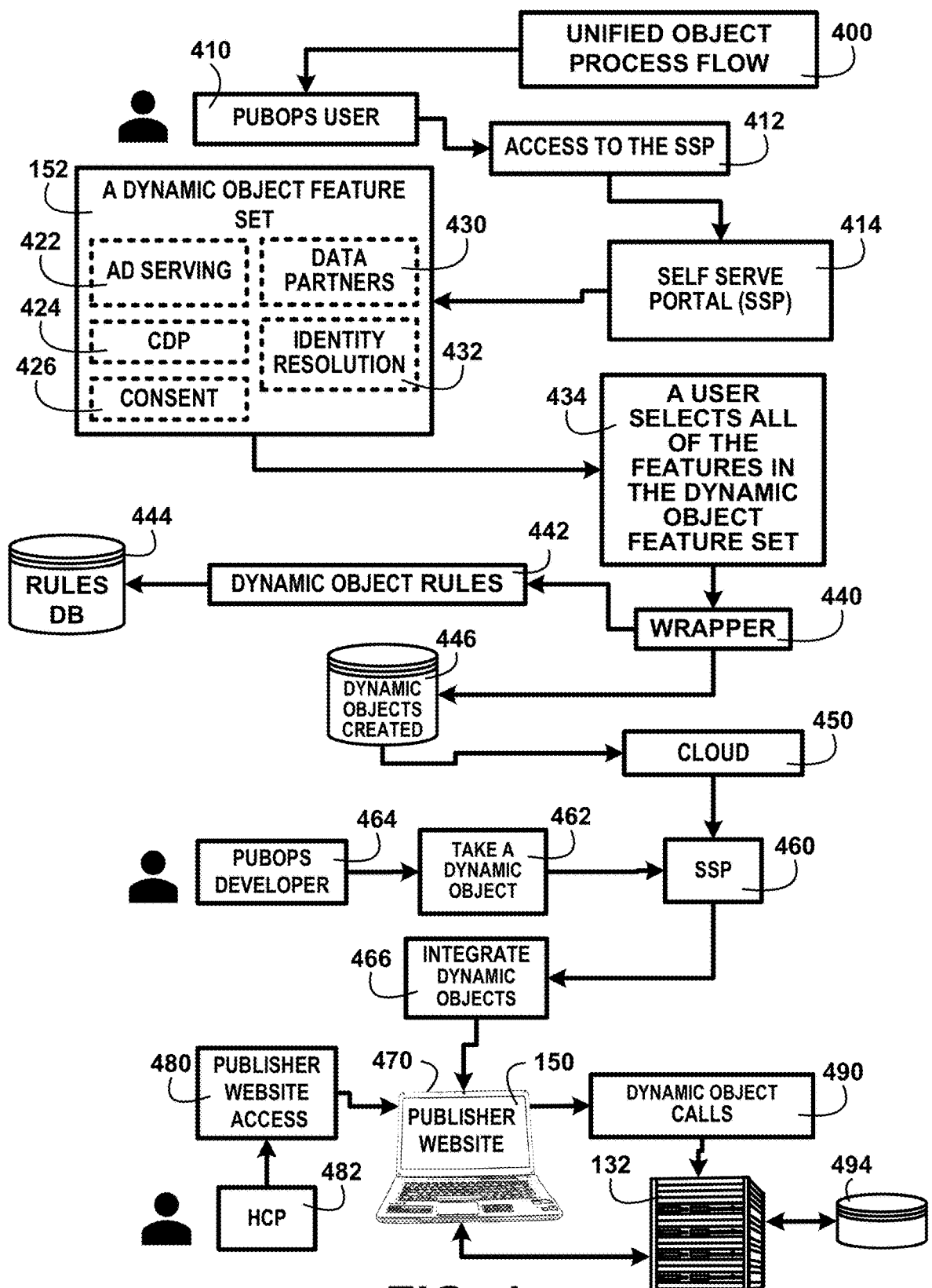
FIG. 4 shows for illustrative purposes only an example of the unified object process flow of one embodiment.

Unified Object Process Flow:

FIG. 4 shows for illustrative purposes only an example of the unified object process flow of one embodiment. FIG. 4 shows a unified object process flow 400 that begins publishing operations and gets access to SSP 412. The SSP is the self-serve portal (SSP) 414 having a dynamic object feature set 152. In this embodiment, the dynamic object feature set 152 includes an ad serving 422, CDP 424 a customer data platform, consent 426 services, data partners 430, and identity resolution 432. In this example, a user selects all of the features in the dynamic object feature set 434. A wrapper 440 retrieves the dynamic object rule 442 from the rules DB 444. The dynamic object features are processed according to the dynamic object rules 442 resulting in dynamic objects created 446. Every Publisher is provided with a set of feature components to choose from. They can consolidate an automated dynamic object from these components to meet their specific requirements.

The dynamic objects created 446 are stored in a cloud 450 and are available in the SSP 460. A pubops developer 464 can take a dynamic object 462 to integrate dynamic object 466 into the computer 470 publisher website 150 having integrated unified dynamic objects 176 of FIG. 1B. The HCP 482 gains publisher website access 480 through the server 132. The publisher website 150 of FIG. 1B loads dynamic object calls 490 through the server 132 from a database 494 of one embodiment.

Figure 5:
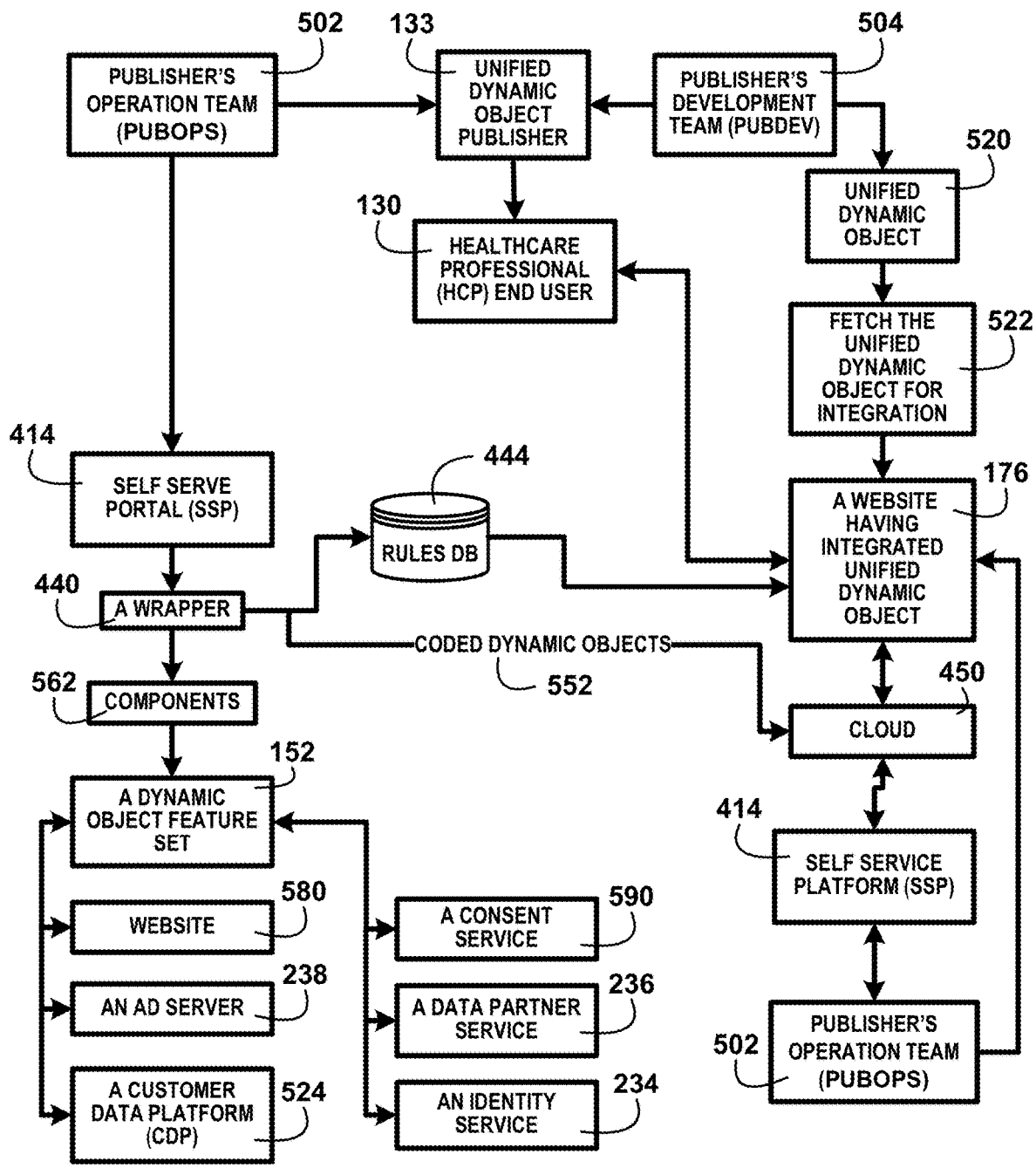
FIG. 5 shows for illustrative purposes only an example of a unified dynamic object publisher of one embodiment.

Unified Dynamic Object Publisher:

FIG. 5 shows for illustrative purposes only an example of a unified dynamic object publisher of one embodiment. FIG. 5 shows a publisher's operation team (pubops) 502 and a publisher's development team (pubdev) 504 that work in the unified dynamic object publisher 133 to assist a healthcare professional (HCP) end user 130. The unified dynamic object publisher 133 operates with publisher selections to customize the publisher website 150 of FIG. 1B. The publisher's development team (pubdev) 504 selects a unified dynamic object 520. The publisher's development team (pubdev) 504 proceeds to fetch the unified dynamic object for integration 522 into the publisher website 150 of FIG. 1B having one or more integrated unified dynamic object 176. In one embodiment the unified dynamic object publisher 260 of FIG. 2 customizes websites meant for healthcare professionals (HCPs).

The publisher's operation team (pubops) 502 enters the self-serve portal (SSP) 414. In the SSP the publisher's operation team (pubops) 502 uses a wrapper 440 to review the rules DB 444 related to the publisher website 150 of FIG. 1B having an integrated unified dynamic object 176. The wrapper 440 provides access to coded dynamic objects 552 stored in the cloud 450. The wrapper 440 provides access to components 562 in a feature set. In this example, component 562 includes the unique set of components configured for the website that meet the specific requirements. In this embodiment, the feature set 152 includes the specific requirements of the website 580 including an ad server 238, a customer data platform (CDP) 524, a consent service 590, a data partner service 236, and an identity service 234. The publisher's operation team (pubops) 502 stores the selected component features in the cloud 450. The self-service platform (SSP) 414 provides access to the cloud 450 to allow the publisher's operation team (pubops) 502 to prepare the selected component features to operate on the website having integrated unified dynamic object 520 of one embodiment.

Figure 6:
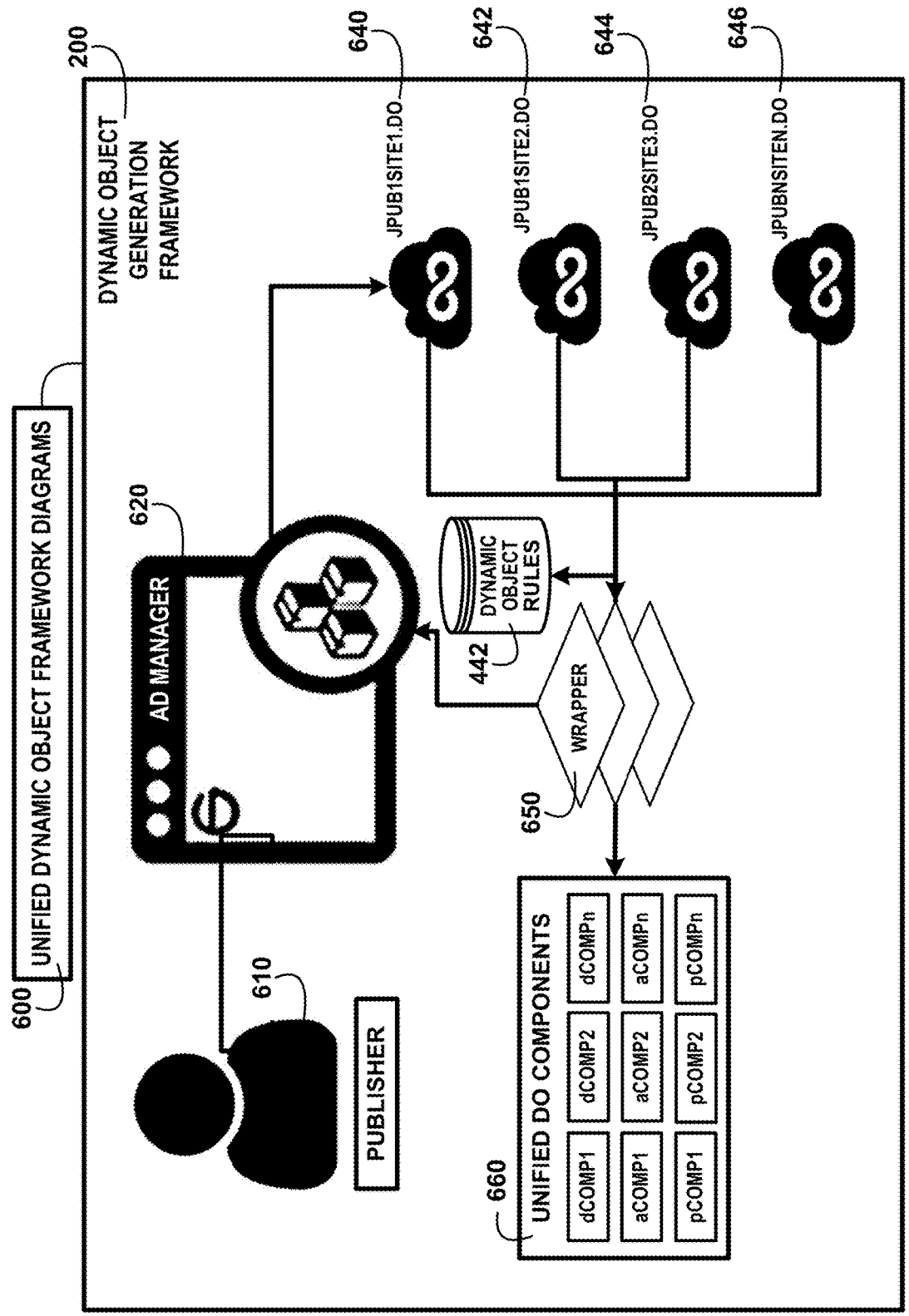
FIG. 6 shows for illustrative purposes only an example of unified dynamic object framework diagrams of one embodiment.

Unified Dynamic Object Framework Diagrams:

FIG. 6 shows for illustrative purposes only an example of unified dynamic object framework diagrams of one embodiment. FIG. 6 shows unified dynamic object framework diagrams 600 including at least one example of a dynamic object generation framework 200. The wrapper/service allows the creation and maintenance of Publisher-specific dynamic object variants within the Unified Dynamic Object Framework 200 of FIG. 2 itself. For example, the framework would facilitate the user to create a specific version of the main Unified Dynamic Object for publisher1, publisher2, . . . publisherN based on specific needs and data collection requirements of every Publisher partner who is integrated with the platform. In this example, publisher 610 utilizes the ad manager 620 to create jpub1site1.do 640, jpub1site2.do 642, jpub2site3.do 644, and jpubnsiten.do 646. The publisher 610 applies the dynamic object rules 442 available through the wrapper 650 to establish the unified DO components 660 for the specific unique website of one embodiment.

Figure 7:
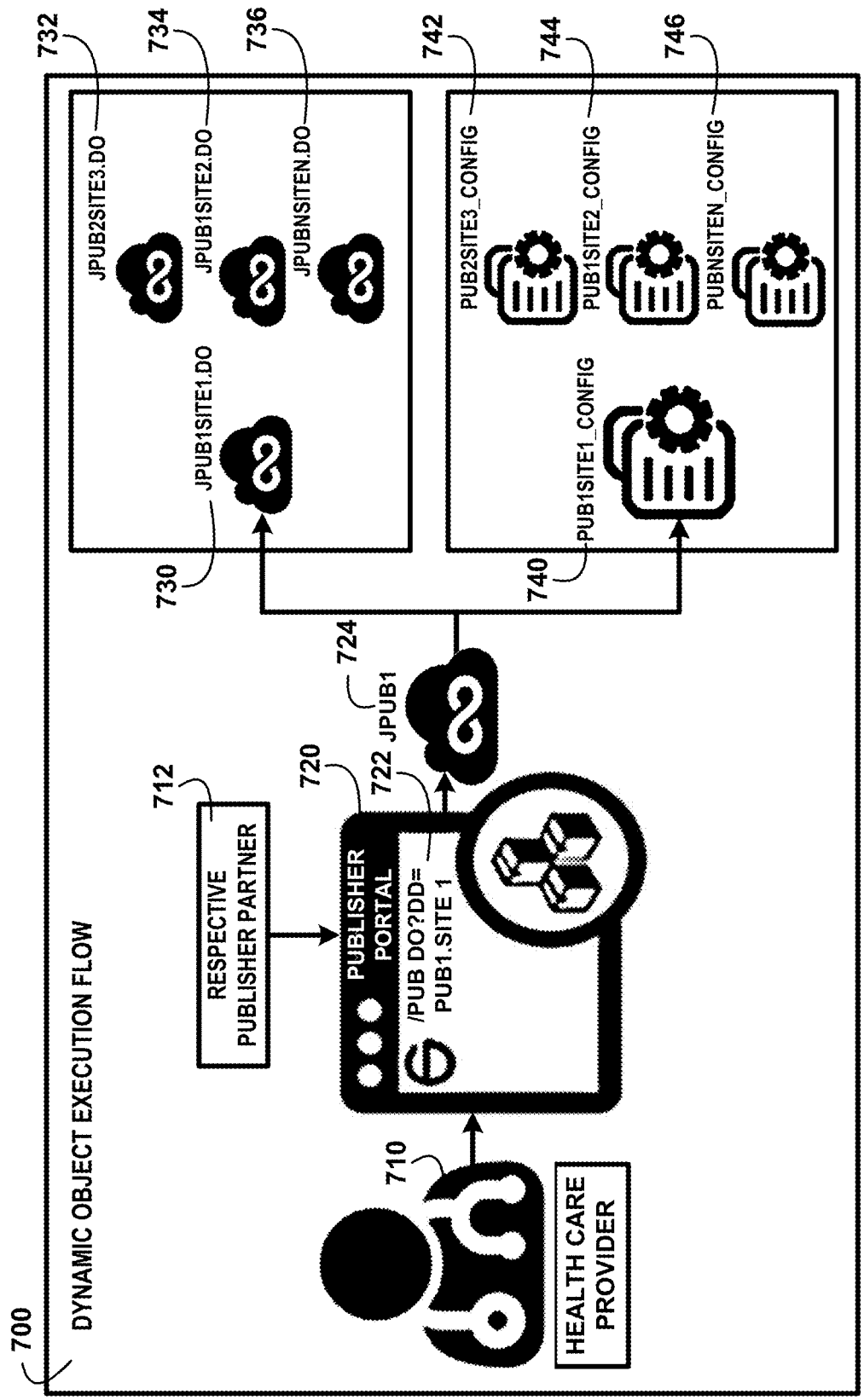
FIG. 7 shows for illustrative purposes only an example of the dynamic object execution flow of one embodiment.

Dynamic Object Execution Flow:

FIG. 7 shows for illustrative purposes only an example of the dynamic object execution flow of one embodiment. FIG. 7 shows at least one dynamic object execution flow 700. The health care provider 710 accesses the publisher portal 720 with an ID for /pub do?dd=pub1.site 1 722. The publisher portal 720 accesses the jpub1 cloud 724. The jpub1 cloud 724 opens up the ID-accessible website and dynamic object files. The health care provider 710 may access the authorized websites associated with the health care provider 710 for example, any or all of jpub1site1.do 730, jpub2site3.do 732, jpub1site2.do 734, and up to jpubnsiten.do 736. Wherein the last site n is the last webpage visited by the authorized health care provider 710.

Once in a particular publisher website 150 of FIG. 1B the unified dynamic object publisher 133 of FIG. 1B may create additional dynamic objects with instructions including pub1site1_config 740, pub2site3_config 742, pub1site2_config 744, and pubnsiten_config 746 of one embodiment. The particular publisher website 150 of FIG. 1B created by the respective publisher partner 712 is in a post-deployment phase of the dynamic object execution. The coded dynamic objects 552 of FIG. 5 stored in the cloud 450 of FIG. 4 have been loaded into the particular publisher website 150 of FIG. 1B at this time.

In this example, the user is primarily an HCP (Health Care Professional) accessing the publisher website 150 of FIG. 1B page(s) where the said unified dynamic object code has already been deployed/integrated by the respective publisher partner 712. The user visit to the publisher website 150 of FIG. 1B triggers a response from the said website page(s) visited by the concerned HCP. The response, from the said publisher website 150 of FIG. 1B, is generated by the automated dynamic object generator 170 of FIG. 1B and the website pair mentioned within the "cid" variable, of the standard URL, that is, "pub.do" associated with that particular publisher website 150 of FIG. 1B and its pages.

As soon as server 132 of FIG. 1B receives the Publisher ID and the Site ID, for example "/pub.do?cid=publisher1:site1", which represents Site 1 associated with publisher 1 makes a call to server 132 of FIG. 1B, the generic "pub.do" notifies the server to respond with the corresponding dynamic object file, for example, "publisher1site1.do".

After locating the required, "publisher1site1.do" file, the "pub.do" concurrently accesses server 132 of FIG. 1B. This time the "pub.do," identifies the corresponding configuration file, that is "publisher1site1_config", which encompasses all the required components/rules that were already set up for publisher 1 and website 1 within the self-serve portal. Once the "publisher1site1_config" file is identified, it fetches the corresponding dynamic object file, that is, "publisher1site1.do".

The identified "publisher1site1.do" is now sent back to the generic "pub.do," which then responds, to the website, with the configured components/rules as mentioned within "publisher1site1.do," thereby completing the entire dynamic object utilization process of the unified dynamic object framework 200 of FIG. 2.

Here the entire process of generating and serving/providing the required components/rules to the respective publisher partner 712 is being done dynamically. Moreover, the engagement with the publisher websites is being driven in its entirety by the dynamic object repository (database) or rules engine. The purpose behind creating the unified dynamic object framework 200 of FIG. 2 is to completely do away with the erstwhile mechanism of creating coded or custom-built dynamic objects, which was a complex task and was completely dependent on human intervention. Moreover, the task of maintaining such complex configurations and including, for example, an exponential number of publisher partners has now been done away with and replaced by workings of the automated unified dynamic object framework 200 of FIG. 2.

Figure 8:
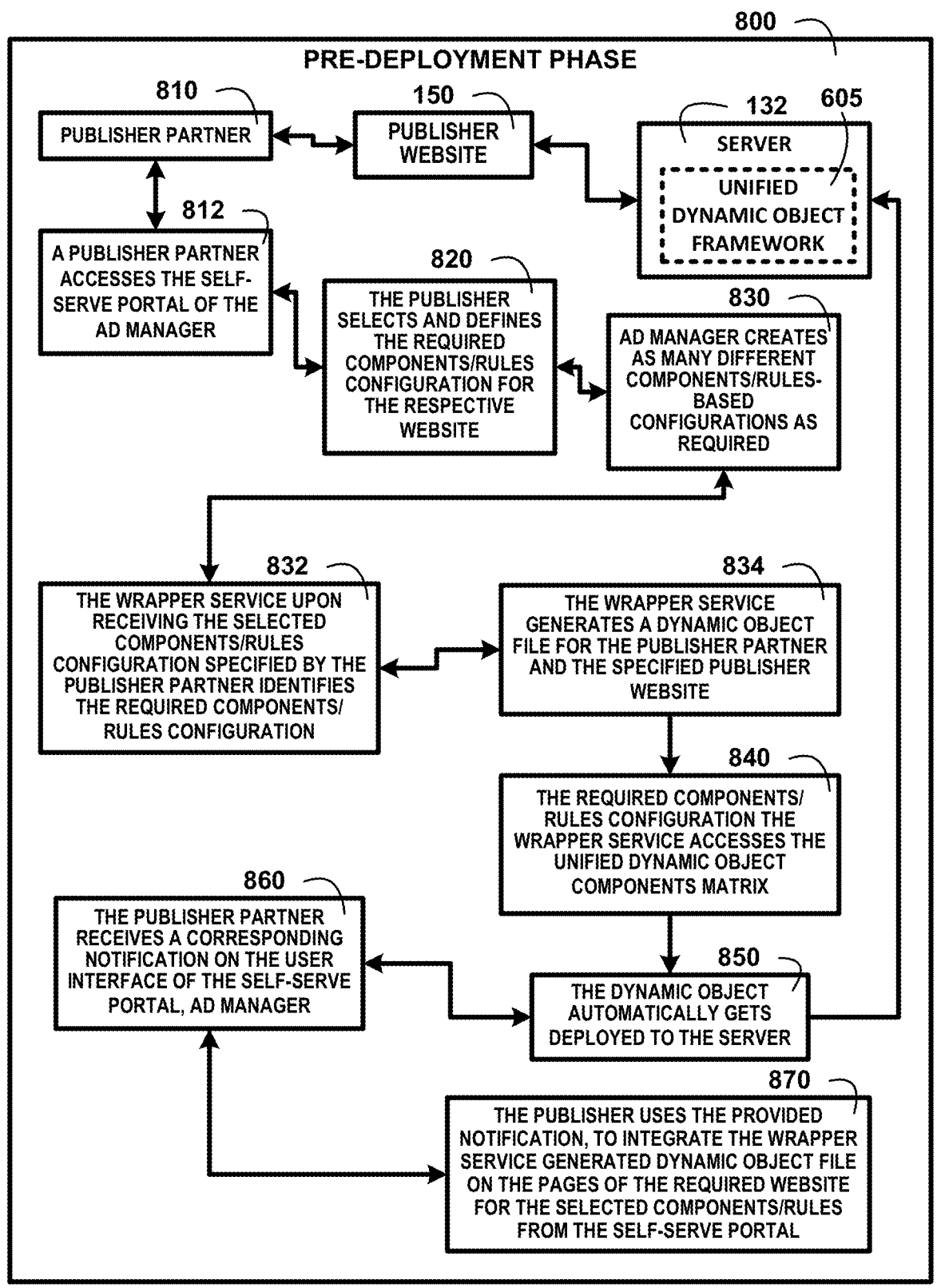
FIG. 8 shows a block diagram of an overview of a pre-deployment phase of one embodiment.

A Pre-Deployment Phase:

FIG. 8 shows a block diagram of an overview of a pre-deployment phase of one embodiment. FIG. 8 shows the pre-deployment phase 800 of the dynamic object generation process flow. A publisher partner 810 has a publisher website 150 and can load the unified dynamic object framework 200 of FIG. 2 from the server 132. The publisher partner accesses the self-serve portal of the ad manager 812 of the unified dynamic object framework 200 of FIG. 2. The self-serve portal guides the partner to select the components to fit the unique publisher partner's needs.

The publisher selects and defines the required components/rules configuration for the respective website 820. Publisher partners will select any combination of components on the self-serve portal, thereby creating the required mix of components/rules to apply to the specific website. Ad manager creates as many different components/rules-based configurations as required 830.

The Unified Dynamic object Framework supports a mapping entity between a single Publisher and a single website, at any given point in time. This means that a certain Publisher, for example, Publisher A can only define components/rules for website A. However, website B can be owned and managed by the same Publisher A while creating a separate set of components/rules-based configuration within the Unified Dynamic object Framework to cater to their new mapping entity, which in this instance will be for Publisher A: website B.

Publisher A can proceed within the self-serve portal, Ad Manager and create as many different components/rules-based configurations as required for mapping entities, for example, Publisher A: website A; Publisher A: website B, Publisher A: website C, . . . Publisher A: website N. The Unified Dynamic object Framework is facilitating the Publisher, that is, Publisher A in this example may pick and choose the required components/rules for the respective websites, using the same codebase.

In this example, Publisher A creates three component/rule configurations for the three websites namely: website A, website B, and website C. Publisher A for website A, might select a set of components/rules-based configurations comprising components, for example, data collection, ad serving, and viewability. For website B Publisher A might only choose data collection and ad serving as the required components/rules. Publisher A may for website C select components/rules, for example, data collection, ad serving, data partner sync, identity partner sync, and viewability.

Publisher A, in this example, can create as many components/rules-based configurations as required, wherein a configuration only maps to a single publisher and a single website combination. In this example, as shown will create and select as many components/rules-based configurations for each website separately and independently of one another. The wrapper service upon receiving the selected components/rules configuration specified by the publisher partner identifies the required components/rules configuration 832.

The process continues after the publisher has selected and defined the required components/rules configuration for the respective website, within the Ad Manager. The self-server portal automatically sends the configuration to a wrapper service wherein the configuration is written and maintained within the server. The wrapper service generates a dynamic object file for the publisher partner and the specified publisher website 834.

The wrapper service upon receiving the selected components/rules configuration specified by the Publisher partner, identifies the required components/rules configuration. After identification of the required components/rules configuration, the wrapper service accesses the Unified Dynamic object Components Matrix. The wrapper service enables only the specific components/rules that the Publisher has selected. For example, if Publisher A has selected components, for example, data collection, ad serving, and viewability, then these very components would be enabled. Only the enabled selected components are processed by the wrapper service, leaving all other non-enabled components within the Unified Dynamic object Components Matrix.

The required components/rules configuration of the wrapper service accesses the unified dynamic object components matrix 840. After marking the enabled required components from the Unified Dynamic object Components Matrix, the wrapper service then stores the enabled/selected components/rules configuration within the Dynamic object rules repository database. The wrapper service generates a Dynamic object file for the Publisher partner and the specified publisher website. The Dynamic object automatically gets deployed to the server 850.

The publisher partner receives a corresponding notification on the user interface of the self-serve portal ad manager 860. The publisher uses the provided notification, to integrate the wrapper service-generated dynamic object file on the pages of the required website for the selected components/rules from the self-serve portal 870.

The Dynamic object code that is generated and deployed on the server is maintained with the respective Publisher and website mapping/pairing. For example, the generated Dynamic object files on the server may have the following nomenclature to specify the Partner and website mapping: "publisher1site1.do," "publisher1site2.do," "publisher1site3.do," "publisher2site1.do", "publisher2site2.do", . . . "publisherNsiteN.do".

The Dynamic object URL that is shared with the respective Publishers remains generic, it is "pub.do" and any custom URL that reads something like this: "publisher1site1.do," "publisher1site2.do", and so forth with the Publisher partners is not shared with other publisher partners.

The generic URL that is shared with the respective Publisher partners has a variable named "Cid". The "cid" designation holds the Publisher and website mapping using the Publisher ID and the Site ID, for example, "/pub.do?cid=publisher1:site1", represents Site 1 is associated with Publisher 1.

This added "cid" designation is used to identify which Dynamic object file's components/rules are required to be served/provided to which Publisher partners and specifically to which particular website of the Publisher partner. The publisher can use the provided notification, to integrate the wrapper service-generated Dynamic object file on the pages of the required website for the selected components/rules from the self-serve portal.

This completes the process of generating a Unified Dynamic object file for a Publisher partner. The publisher can dynamically select the required components/rules and the Unified Dynamic object Framework automatically configures the required components/rules and generates the Unified Dynamic object for integration into the respective website when the Publisher plans to meet the requirements of the website. The Publisher can repeat the process, and create additional Dynamic object code for other of the Publisher websites as required that are utilizing the Unified Dynamic object Framework of one embodiment.

Figure 9:
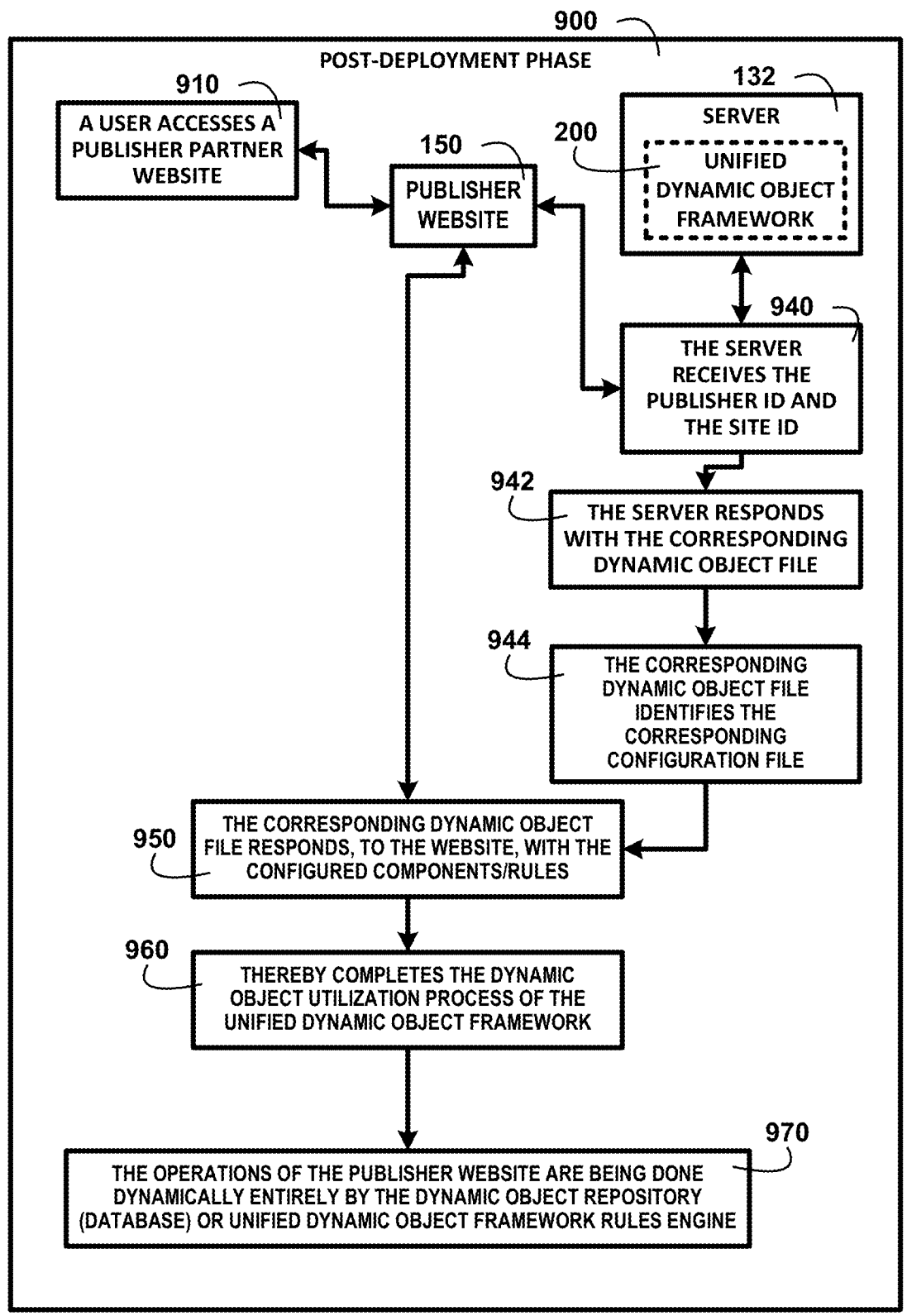
FIG. 9 shows a block diagram of an overview of a post-deployment phase of one embodiment.

A Post-Deployment Phase:

FIG. 9 shows a block diagram of an overview of a post-deployment phase of one embodiment. FIG. 9 shows a post-deployment phase 900 wherein a user accesses a publisher partner website 910. The following represents the post-deployment phase dynamic object execution process flow. The publisher website 150 is wirelessly coupled to the server 132 having the unified dynamic object framework 200. First, step 1 of the post-deployment phase of the dynamic object execution process takes place on a website where the Unified Dynamic object code has already been deployed/integrated by a respective Publisher partner. A user, in this example, is primarily a Health Care Professional (HCP) accessing the website page(s) of the Publisher partner website.

The user's visit to the required publisher partner website triggers a response from the website page(s) visited by the concerned HCP. The response, from the site, is generated by the Publisher and website pair mentioned within the "cid" variable, of the standard URL, that is, "pub.do" associated with that particular website and its pages. The server receives the publisher ID and the site ID 940.

The receipt by the server of the Publisher ID and the Site ID in a "cid" variable, of the standard URL, for example, "/pub.do?cid=publisher1:site1", the generic "pub.do" notifies the server to respond with the corresponding Dynamic object file. The "/pub.do?cid=publisher1:site1" call represents Site 1 associated with Publisher 1. The server response, in this example, to the call to the server, triggers the generic "pub.do" to respond with the corresponding Dynamic object file, that is in this example, "publisher1site1.do".

The server responds with the corresponding dynamic object file 942. The corresponding dynamic object file identifies the corresponding configuration file 944. After locating the required, "publisher1site1.do" file, the "pub.do" concurrently accesses the server. The generic "pub.do," identifies the corresponding configuration file, that is "publisher1site1_config", which encompasses all the required components/rules that were already set up for Publisher 1 and Website 1 within the self-serve portal. Once the "publisher1site1_config" file is identified, it fetches the corresponding Dynamic object file, that is, "publisher1site1.do".

The corresponding dynamic object file responds, to the website, with the configured components/rules 950. Fourth, in step 4, the identified "publisher1site1.do" is now sent back to the generic "pub.do," which then responds, to the website, with the configured components/rules within "publisher1site1.do". The transmission of the configured components/rules within "publisher1site1.do" thereby completes the Dynamic object utilization process of the Unified Dynamic object Framework. Thereby completes the dynamic object utilization process of the unified dynamic object framework 960.

The operations of the publisher website are being done dynamically entirely by the dynamic object repository (database) or unified dynamic object framework rules engine 970. The entire process of generating, serving, and providing the required components/rules to the Publisher partners is being done dynamically. The operations of the Publisher website are being done entirely by the Dynamic object repository (database) or Unified Dynamic object Framework rules engine.

The functions of the Unified Dynamic Object Framework are completed with minimal human intervention. The minimal human intervention is the initial user's visit to the required publisher partner website that triggers the dynamic functions of the Unified Dynamic object Framework automatically of one embodiment.

The foregoing has described the principles, embodiments, and modes of operation of the present invention. However, the invention should not be construed as being limited to the particular embodiments discussed. The above-described embodiments should be regarded as illustrative rather than restrictive, and it should be appreciated that variations may be made in those embodiments by workers skilled in the art without departing from the scope of the present invention as defined by the following claims.

What is claimed is:

1. A dynamic unified object generation platform, comprising:
    a dynamic unified object generation computer server coupled to at least a first partner and a second partner and configured to electronically receive and store in a server database at least a first set of rules from the first partner and a second set of rules from the second partner for a publisher website;
    a server processor coupled to the server database and configured to automatically and dynamically create a comparison between a unified set of rules and the first set of rules and the second set of rules;
    a pre-deployment processor coupled to the server processor and configured to dynamically convert the comparison into a single unified code structure based on the unified set of rules;
    a post-deployment processor coupled to the pre-deployment processor and configured to dynamically integrate the single unified code structure into the publisher website as a unified rule set to control at least two predetermined operational aspects of the publisher website based on the first and second set of rules; and
    at least one graphical user interface configured to display to a publisher user of the publisher website at least one operational aspect controlled by the unified rule set.

2. The dynamic unified object generation platform of claim 1, wherein at least one operational aspect includes a targeted advertisement configured to be displayed to the publisher user from the first partner based on the first rule set and controlled by the unified rule set.

3. The dynamic unified object generation platform of claim 1, wherein at least one operational aspect includes a targeted advertisement configured to be displayed to the publisher user from the second partner based on the second rule set and controlled by the unified rule set.

4. The dynamic unified object generation platform of claim 1, further comprising a historical page URL data database coupled to the server configured to store a collection of end user web pages searched that identifies the end user's areas of interest.

5. The dynamic unified object generation platform of claim 1, wherein the first set of rules has selected components including data collection, ad serving, and viewability, then these selected components would be enabled.

6. The dynamic unified object generation platform of claim 1, further comprising a self-serve portal coupled to the server configured to allow access to a publisher to select components and rules to generate dynamic objects.

7. The dynamic unified object generation platform of claim 1, further comprising a unified dynamic object framework rules engine configured to receive from the dynamic unified object generation computer server a publisher website ID and site ID to determine a corresponding dynamic object file with components and rules, wherein the components and rules are dynamically transmitted to the publisher website.

8. A dynamic unified object generation platform, comprising:
    a dynamic unified object generation computer server coupled to at least a first partner and a second partner and configured to electronically receive and store in a server database at least a first set of rules from the first partner and a second set of rules from the second partner for a publisher website;
    a self-serve portal coupled to the server configured to allow access to a publisher to select components and rules to generate dynamic objects
    a server processor coupled to the server database and configured to automatically and dynamically create a comparison between a unified set of rules and the first set of rules and the second set of rules;
    a pre-deployment processor coupled to the server processor and configured to dynamically convert the comparison into a single unified code structure based on the unified set of rules;
    a post-deployment processor coupled to the pre-deployment processor and configured to dynamically integrate the single unified code structure into the publisher website as a unified rule set to control at least two predetermined operational aspects of the publisher website based on the first and second set of rules; and
    at least one graphical user interface configured to display to a publisher user of the publisher website at least one operational aspect controlled by the unified rule set.

9. The dynamic unified object generation platform of claim 8, wherein at least one operational aspect includes a targeted advertisement configured to be displayed to the publisher user from the first partner based on the first rule set and controlled by the unified rule set.

10. The dynamic unified object generation platform of claim 8, wherein at least one operational aspect includes a targeted advertisement configured to be displayed to the publisher user from the second partner based on the second rule set and controlled by the unified rule set.

11. The dynamic unified object generation platform of claim 8, further comprising a historical page URL data database coupled to the server configured to store a collection of end user web pages searched that identifies the end user's areas of interest.

12. The dynamic unified object generation platform of claim 8, wherein the first set of rules has selected components including data collection, ad serving, and viewability, then these selected components would be enabled.

13. The dynamic unified object generation platform of claim 8, further comprising a self-serve portal coupled to the server configured to allow access to a publisher to select components and rules to generate dynamic objects.

14. The dynamic unified object generation platform of claim 8, further comprising a unified dynamic object framework rules engine configured to receive from the dynamic unified object generation computer server a publisher website ID and site ID to determine a corresponding dynamic object file with components and rules, wherein the components and rules are dynamically transmitted to the publisher website.

15. A dynamic unified object generation platform, comprising:
    a dynamic unified object generation computer server coupled to at least a first partner and a second partner and configured to electronically receive and store in a server database at least a first set of rules from the first partner and a second set of rules from the second partner for a publisher website;
    a server processor coupled to the server database and configured to automatically and dynamically create a comparison between a unified set of rules and the first set of rules and the second set of rules;

a pre-deployment processor coupled to the server processor and configured to dynamically convert the comparison into a single unified code structure based on the unified set of rules;

a post-deployment processor coupled to the pre-deployment processor and configured to dynamically integrate the single unified code structure into the publisher website as a unified rule set to control at least two predetermined operational aspects of the publisher website based on the first and second set of rules;

a unified dynamic object framework rules engine configured to receive from the dynamic unified object generation computer server a publisher website ID and site ID to determine a corresponding dynamic object file with components and rules, wherein the components and rules are dynamically transmitted to the publisher website; and at least one graphical user interface configured to display to a publisher user of the publisher website at least one operational aspect controlled by the unified rule set.

16. The dynamic unified object generation platform of claim 15, wherein at least one operational aspect includes a targeted advertisement configured to be displayed to the publisher user from the first partner based on the first rule set and controlled by the unified rule set.

17. The dynamic unified object generation platform of claim 15, wherein at least one operational aspect includes a targeted advertisement configured to be displayed to the publisher user from the second partner based on the second rule set and controlled by the unified rule set.

18. The dynamic unified object generation platform of claim 15, wherein the first set of rules has selected components including data collection, ad serving, and viewability, then these selected components would be enabled.

19. The dynamic unified object generation platform of claim 15, further comprising a self-serve portal coupled to the server configured to allow access to a publisher to select components and rules to generate dynamic objects.

20. The dynamic unified object generation platform of claim 15, further comprising a self-serve portal coupled to the server configured to allow access to a publisher to select components and rules to generate dynamic objects.

* * * * *